(12) United States Patent
Hong

(10) Patent No.: US 8,343,180 B2
(45) Date of Patent: Jan. 1, 2013

(54) SAFETY LANCET FOR PREVENTING REUSE

(76) Inventor: Kwan Ho Hong, Gwangmyeong-si (KR)

(*) Notice: Subject to any disclaimer, the term of this patent is extended or adjusted under 35 U.S.C. 154(b) by 255 days.

(21) Appl. No.: 12/906,248

(22) Filed: Oct. 18, 2010

(65) Prior Publication Data

US 2011/0144682 A1 Jun. 16, 2011

(30) Foreign Application Priority Data

Dec. 14, 2009 (KR) .................. 10-2009-0123912

(51) Int. Cl.
*A61B 17/32* (2006.01)
(52) U.S. Cl. ........................................ 606/182
(58) Field of Classification Search .......... 606/181–183, 606/167, 185–189; 600/573, 583; 604/110, 604/136–138; 30/151, 335–339
See application file for complete search history.

(56) References Cited

U.S. PATENT DOCUMENTS

| | | | | |
|---|---|---|---|---|
| 6,730,046 | B1* | 5/2004 | Hamamoto et al. | 600/583 |
| 7,713,280 | B2* | 5/2010 | Marshall et al. | 606/181 |
| 2002/0077650 | A1* | 6/2002 | Schraga | 606/182 |
| 2004/0092997 | A1* | 5/2004 | Levin et al. | 606/181 |
| 2005/0234487 | A1* | 10/2005 | Shi | 606/181 |
| 2006/0116705 | A1* | 6/2006 | Schraga | 606/181 |
| 2006/0253146 | A1* | 11/2006 | Marshall et al. | 606/182 |

FOREIGN PATENT DOCUMENTS

| | | |
|---|---|---|
| KR | 1020000068203 A | 11/2000 |
| KR | 200315777 Y1 | 5/2003 |
| KR | 1020010025185 A | 3/2005 |
| WO | 2004/080305 A1 | 9/2004 |

* cited by examiner

*Primary Examiner* — Ryan Severson
*Assistant Examiner* — David Eastwood
(74) *Attorney, Agent, or Firm* — LRK Patent Law Firm

(57) ABSTRACT

A safety lancet for preventing reuse is provided, including an upper and lower case, moving block, guide, pressing plate, seating recess, and resilient spring. The upper case and a lower cases are coupled together with a space therein and a through-hole at the front to expose a lancet needle. The moving block is movable within the cases. with the lancet needle at the front. The guide is positioned behind the moving block within the cases and includes an anti-reverse ledge to selectively restrict reverse movement for reloading of the moving block. The pressing plate is pivotably mounted to the upper case and includes a stopper on which the moving block is caught, and a pressing projection for pressing the guide. The seating recess is defined in a bottom of the lower case, in which the guide descends and is seated. The resilient spring supports the rear of the moving block.

8 Claims, 7 Drawing Sheets

PRIOR ART

SAFETY LANCET FOR PREVENTING REUSE

CROSS-REFERENCE TO RELATED APPLICATION

This application claims the benefit under 35 U.S.C. 119(a) of Korean Patent Application No. 10-2009-0123912, filed on Dec. 14, 2009, the entire disclosure of which is incorporated herein by reference for all purposes.

BACKGROUND

1. Field

The present disclosure relates to a safety lancet, and more particularly, to a safety lancet capable of fundamentally preventing the reuse of lancets for collecting blood, in order to obviate the possibility of infections arising from such reuse.

2. Description of the Related Art

Lancets (blood collecting needles) are generally used in hospitals and other facilities to conveniently collect blood for the purpose of conducting various tests on patients. For example, a lancet is used to apply pressure to capillary subcutaneous tissue of a finger or toe to draw and collect a small amount of blood, which is then used to measure a diabetic patient's blood-sugar level or is input to a blood analysis device for cholesterol, triglyceride (TG), etc. to perform various blood analyses.

Following blood collection, conventional blood collecting devices were often reused after being washed with water or subjected to simple sterilization, which is a serious form of medical malpractice that can cause the transmission of AIDS, hepatitis, and other diseases through tainted blood.

Figure 9:
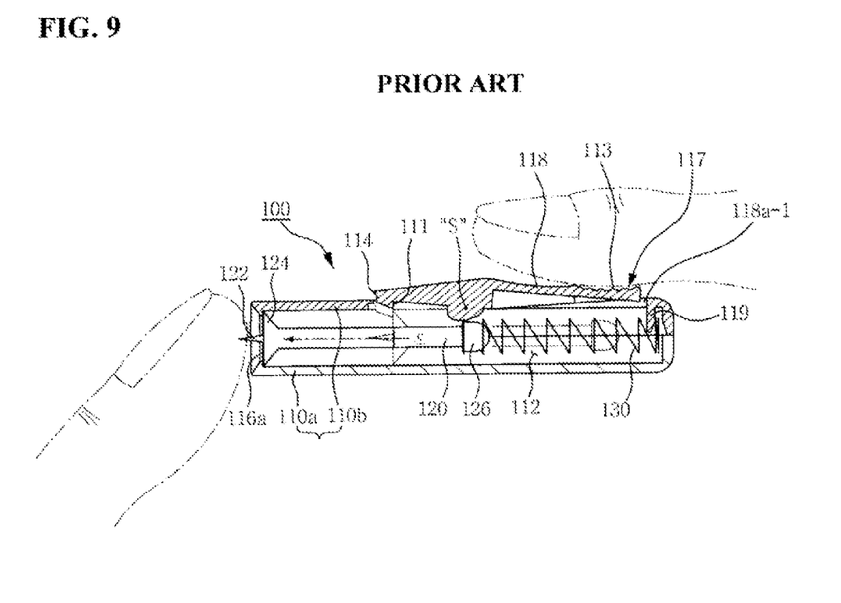
FIG. 9 is a view showing a blood collecting device being used according to the related art.

FIG. 9 is a diagram illustrating a related art disposable automatic blood collecting device 100 developed to prevent its reuse, which includes a housing 110 having a sectional barrel structure, and a lancet needle 120 for collecting blood. The housing 110 is configured with an upper and lower case 110a and 110b capable of being spread apart and closed. With the upper and lower cases 110a and 110b of the house 110 opened, the lancet needle 120 is stored in a storage space 112, and when the installation of the lancet needle 120 is completed, the upper and lower cases 110a and 110b are converged together to complete the product. The storage space 112 is defined within the housing 110 to store the lancet needle 120 for collecting blood. A front wall opening 116a is defined through a portion of a front wall 116 of the housing 110, a top wall opening 118a-1 is defined in the top wall to correspond to the shape of press/release means 118, and the remaining wall portions are sealed inside and out.

The press/release means 118 is provided on a side of the housing 110 to prevent the lancet needle 120 from travelling forward to the front wall opening 116a of the housing 110. The press/release means 118 is provided with a disengagement prevention catch 111 projecting from a side thereof. and a catching ledge 124 formed at the front end of the lancet needle 120 is maintained in a latched state by the disengagement prevention catch 111 to prevent movement of the lancet needle 120. A concave pressing portion 117 is defined at a predetermined position in the press/release means 118, an anti-slip projection 113 is formed projecting in an undulating manner on the top surface of the pressing portion 117, and a portion at the front end of the press/release means 118 is connected at a predetermined location at the top surface wall of the housing by means of a thin film type connecting piece 114.

During use of the above-configured automatic blood collecting device 100, when a user presses the pressing portion 117 of the press/release means 118 towards the top wall opening 118a-1 of the housing 110, the latching of the catching ledge 124 of the lancet needle 120 to the disengagement prevention catch 111 is disengaged so that it travels toward the front wall opening 116a. Here, the lancet needle 120 receives resilient force from a spring 130 provided within the housing 110 and moves forward toward the front wall opening 116a, and the needle 122 moves to the outside of the front wall opening 116a. In the process of pressing the press/release means 118, the thin film type connecting piece 114 connecting the housing 110 and press/release means 118 is disconnected and separates. Therefore, because the press/release means 118 is not returned to its original position, it cannot fix the lancet needle 120, and can thus prevent reuse of the automatic blood collecting device 100.

However, after the above blood collecting device of the related art is used, the disconnected connecting piece 114 may be reconnected to the upper wall of the housing 110 through melting under a certain temperature, making reuse possible.

SUMMARY

To overcome the limitations of the above related art, an object of the present disclosure is to provide a safety lancet structure more capable of fundamentally preventing reuse thereof, in order to effectively prevent accidental infections arising from repeated use on a plurality of persons.

In one embodiment, a safety lancet for preventing reuse includes: an upper case and a lower case coupled to one another to define a space of a certain volume therein, and defining through-holes at a front end thereof to enable a lancet needle to be exposed therethrough; a moving block provided to be movable within the cases and including the lancet needle formed at a front end thereof; a guide disposed at a rear end of the moving block within the cases, and including an anti-reverse ledge at a front end thereof to selectively restrict reverse movement for reloading of the moving block; a pressing plate pivotably mounted to the upper case on a pivot support that is an axis, and including a stopper projecting downward at a front end thereof on which the moving block is caught, and a pressing projection at a rear end thereof for pressing the guide; a seating recess defined in a bottom surface of the lower case, in which the guide that is pressed by the pressing plate descends and is seated; and a resilient spring for supporting the rear end of the moving block with a predetermined resilient force.

Also, the moving block may further include guide projections projecting from either sidewall thereof, and the cases may further include guide grooves defined horizontally in inner walls thereof corresponding to the guide projections to guide the guide projections.

The details of one or more embodiments are set forth in the accompanying drawings and the description below. Other features will be apparent from the description and drawings, and from the claims.

BRIEF DESCRIPTION OF THE DRAWINGS

FIG. 6 shows a safety lancet according to the present disclosure in a loaded state, where FIG. 6A is a lateral sectional view, and FIG. 6B is a frontal sectional view.

FIG. 7 shows a safety lancet according to the present disclosure in a deployed state, where FIG. 7A is a lateral sectional view, and FIG. 7B is a frontal sectional view.

DETAILED DESCRIPTION OF THE EMBODIMENTS

Specific embodiments of the present disclosure will be described in detail below, examples of which are illustrated in the accompanying drawings.

To first describe the overall configuration of a safety lancet according to the present embodiment, with reference to FIGS. 1 through 5, an upper case 10 and a lower case 20 that are coupled together to define a hexahedral inner space and respectively have a semicircular through-hole 11 and 21 defined in corresponding locations at front ends thereof and guide grooves 12 and 22 defined horizontally in the sidewalls.

Also, the cases 10 and 20 have a moving block 30 and guide 40 provided therein to be movable forward and rearward, and a resilient spring 50 installed to impart resilient force to the rear end of the moving block 30. The moving block 30 has a lancet needle 31 formed projecting from the front end thereof, guide projections 32 formed projecting at either sidewall thereof to be guided along the guide grooves 12 and 22, and a cylindrical support projection 35 projecting from the rear end thereof to support the resilient spring 50.

The guide 40 has resilient wings 41 projecting at either side thereof, an anti-reverse ledge 42 provided at the front end of the guide to selectively restrict reversal during reloading of the moving block 30, and a connecting ledge 44 projecting at a lower front side thereof to connect with the moving block 30 and enable forward/reverse movement together with the moving block 30.

A pressing plate 13 is installed on the upper case 10 to be pivotable about an axis of a pivot support 14, a stopper 13a projects downward at the front end of the pressing plate 13 to latch the moving block 30 in loaded mode, and a pressing projection 13b is provided at the rear end for pressing the guide 40.

Figure 1:
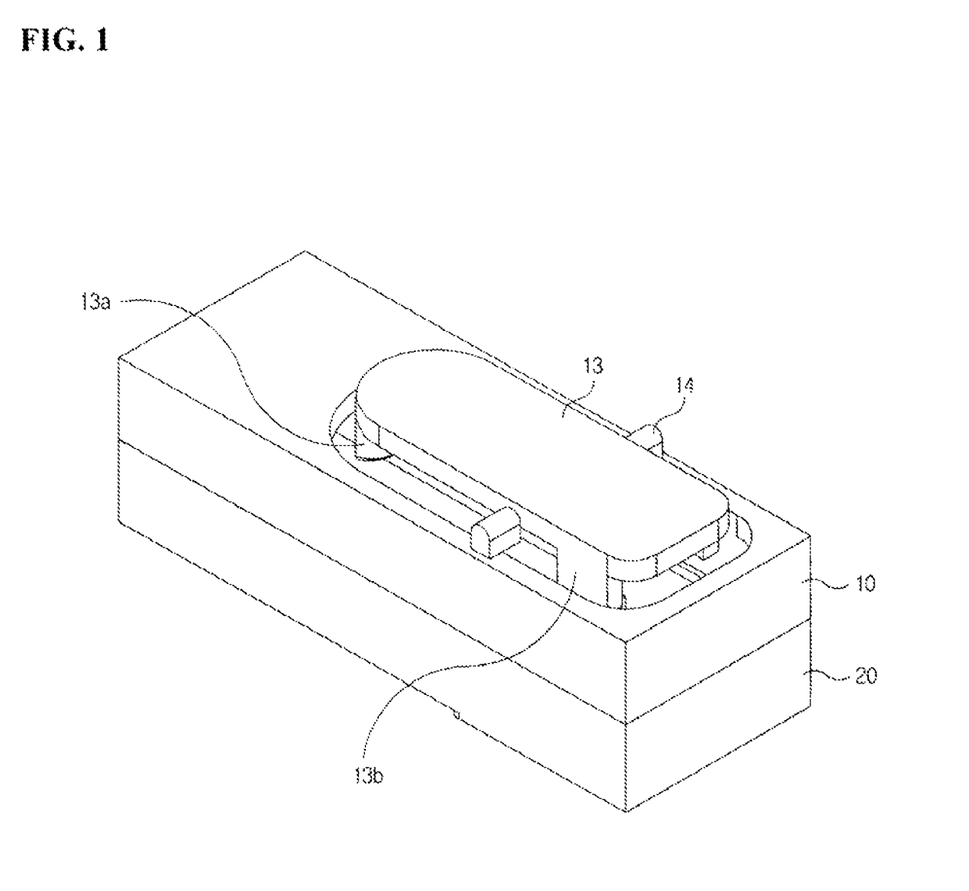
FIG. 1 is a perspective view of a safety lancet according to the present disclosure.
Figure 2:
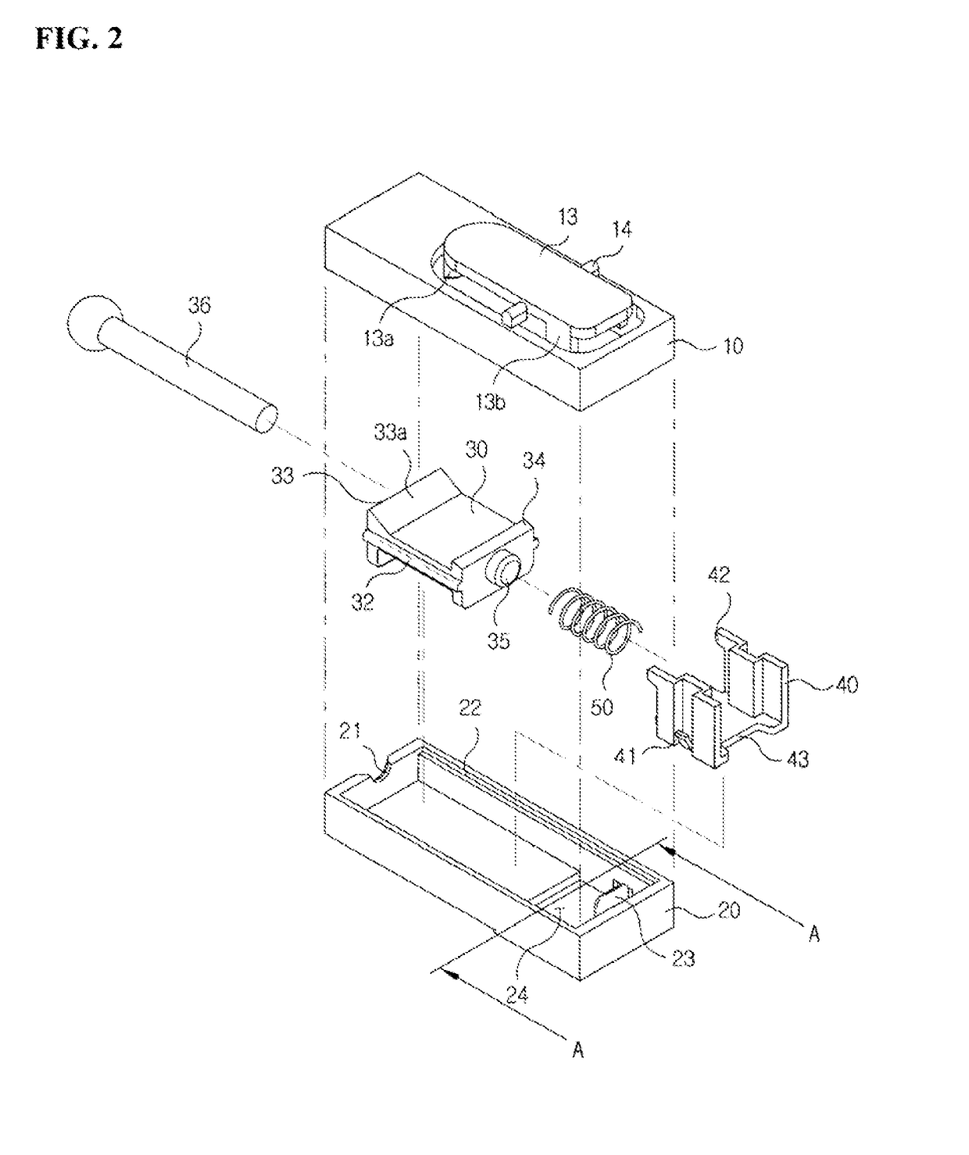
FIG. 2 is a rear exploded perspective view of a safety lancet according to the present disclosure.
Figure 3:
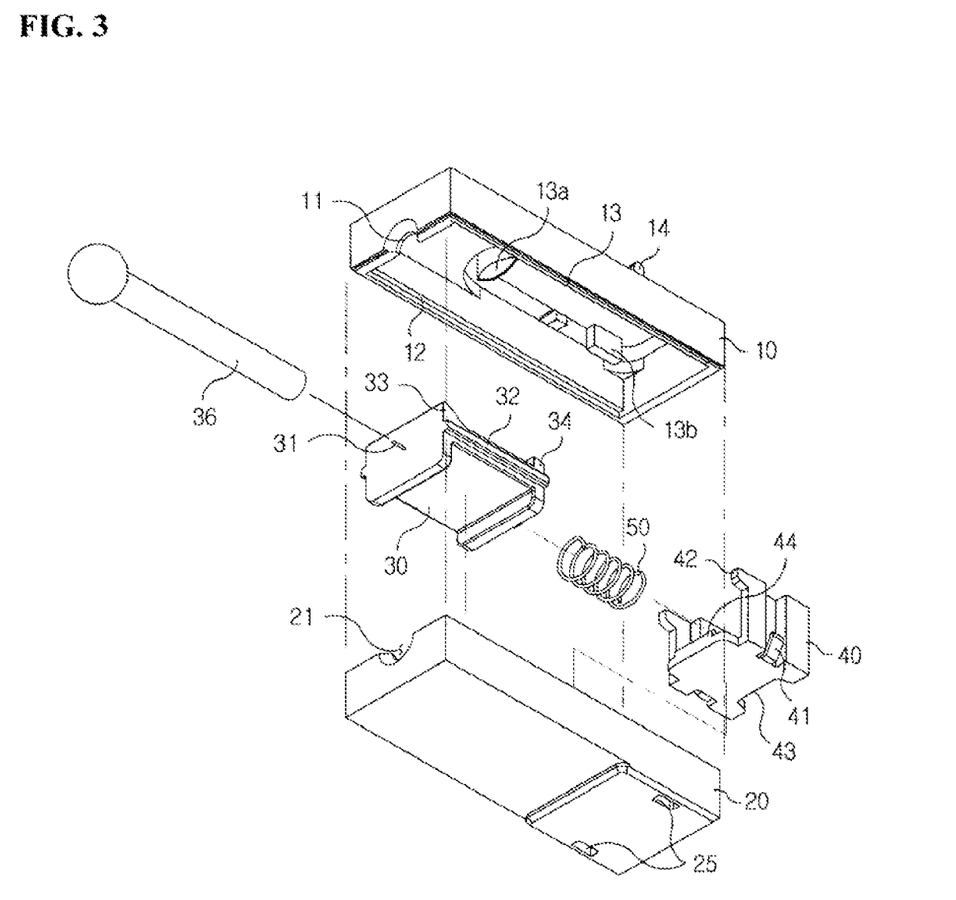
FIG. 3 is an exploded perspective view showing the assembly of a safety lancet according to the present disclosure.
Figure 4:
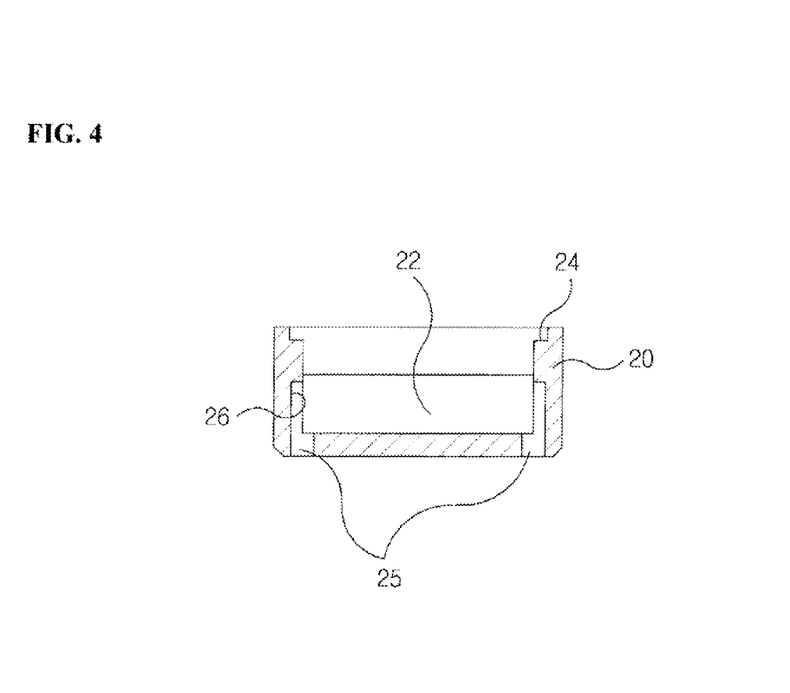
FIG. 4 is a sectional view of FIG. 1.

A seating recess 24 is defined in the lower case 20 so that the guide 40 pressed by the pressing plate 13 can descend and be seated therein; insert holes 26 are defined in the left and right walls of the seating recess 24 for the resilient wings 41 on both sides of the descending guide 40 to catch in as shown in the sectional view of FIG. 4, and positioning holes 25 are defined through the floor to check the ascending or descending position of the guide 40.

A supporting partition 23 for supporting the position of the resilient spring 50 is formed at a certain height at the rear end of the lower case 20, and a recess 43 for preventing interference with the supporting partition 23 during reversal is defined in the rear end of the guide 40.

In addition, a catching ledge 33 is formed on the front upper portion of the moving block 30 for the stopper 13a to catch on, and the top surface of the catching ledge 33 defines an inclined surface 33a of a certain angle to allow the stopper 13a to press against it and easily travel in reverse during reversal of the moving assembly 30.

The effects of using the above-configured safety lancet according to the present disclosure will be discussed with reference to FIGS. 5 through 8.

Figure 5:
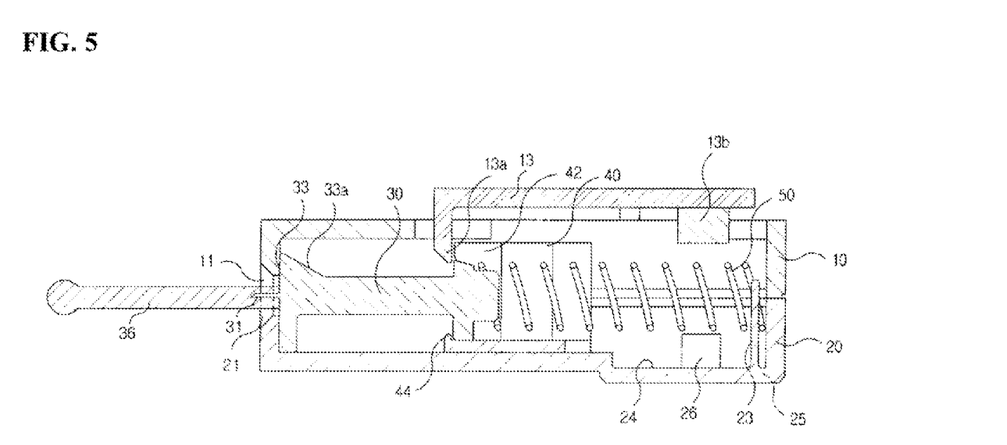
FIG. 5 is a sectional configurative view of a safety lancet according to the present disclosure.

In standby mode prior to loading, as shown in FIG. 5, while the moving block 30 is in a forward position, the guide 40 maintains a connected state with the moving block 30 by means of the connecting ledge 44.

Figure 6A:
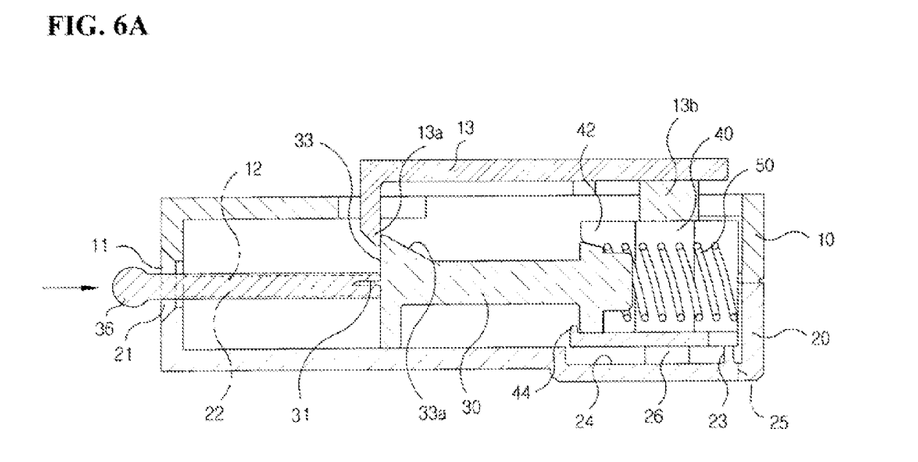
Figure 6B:
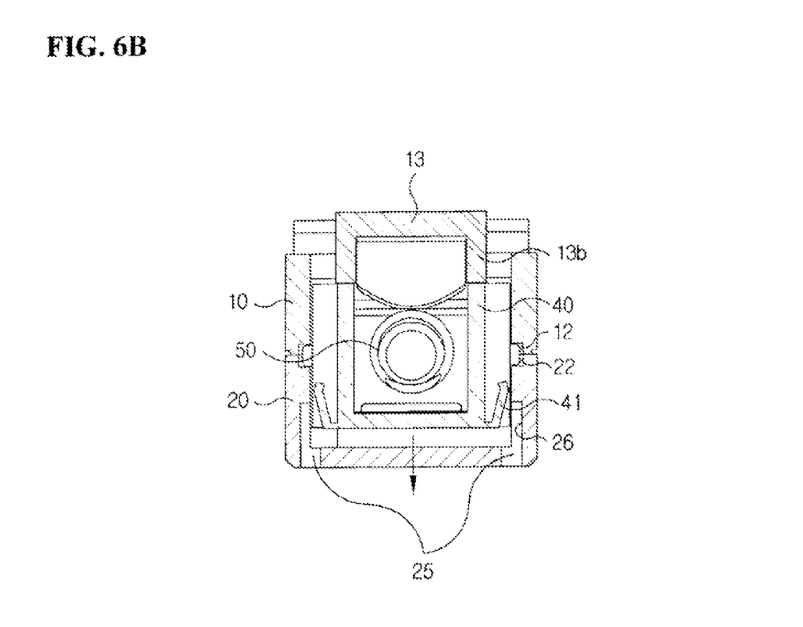

For blood collection in loading mode, when a protective cap (or loading shaft) 36 is pushed into the through-holes 11 and 21 to move the moving block 30 rearward, because the moving block 30 moves rearward in the cases 10 and 20, the guide 40 also moves rearward in concert. Therefore, as the resilient spring 50 is compressed, the catching ledge 33 of the moving block 30 catches on the stopper 13a of the pressing plate 13, and forward movement is restricted in the loaded state shown in FIG. 6.

Figure 7A:
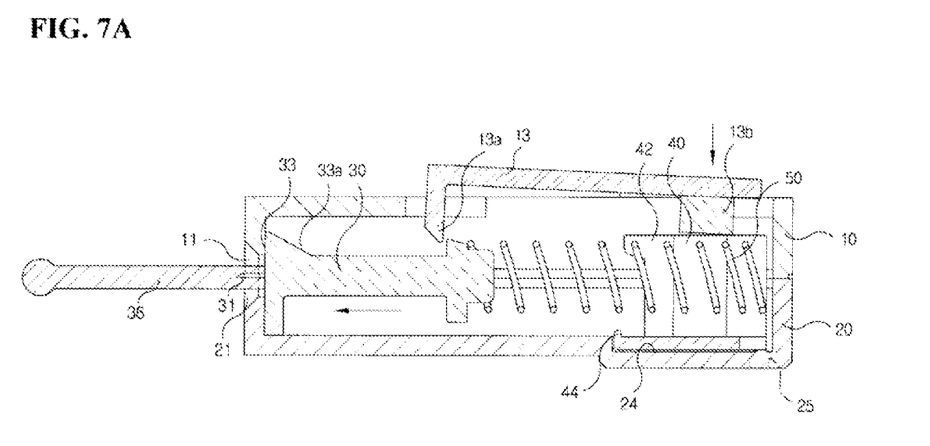
Figure 7B:
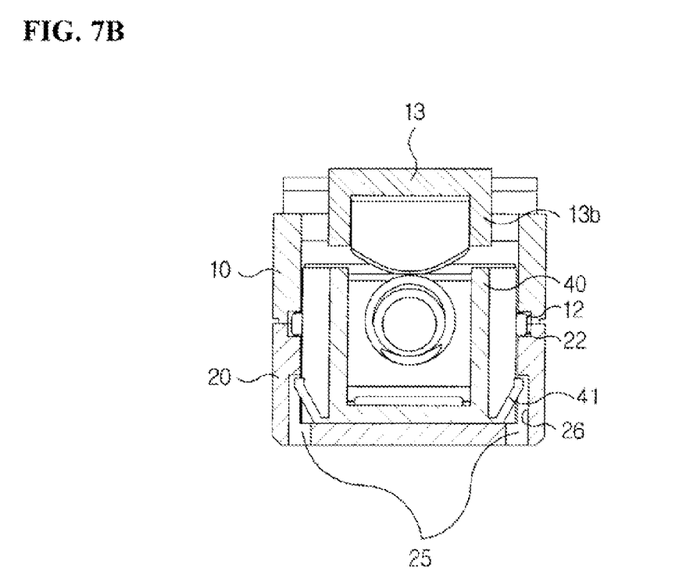

In this state, when a user removes the protective cap 36 and presses the rear of the pressing plate 13 after placing the Through-holes 11 and 21 at a position on the skin for collecting blood, the pressing plate 13 is pivoted toward the pivot support 14 to raise the stopper 13a, so that the moving block 30 whose latched state is released is moved forward by means of the resilient force of the resilient spring 50, and the lancet needle 31 is exposed through the through-holes 11 and 21, as shown in FIG. 7 so that blood collection is performed at the position on the skin in contact.

Here, because the guide projections 32 at either side of the moving block 30 are guided along the guide grooves 12 and 22 of the inner wall, reliable forward movement of the moving block 30 can he secured. and pain at the time the lancet needle 31 penetrates the skin can be reduced.

When the pressing action of the pressing plate 13 is performed, the guide 40 is pressed by the pressing projection 13b and descends and is seated in the seating recess 24 of the lower case 20, so that the connected state with the moving block 30 by means of the connecting ledge 44 is simultaneously negated.

Through the guide 40 descending, the resilient wings 41 at either side are inserted and retained in the insert holes 26 defined in the lower case 20 sidewalls, so that the guide 40 can be prevented from ascending to its original position.

Figure 8:
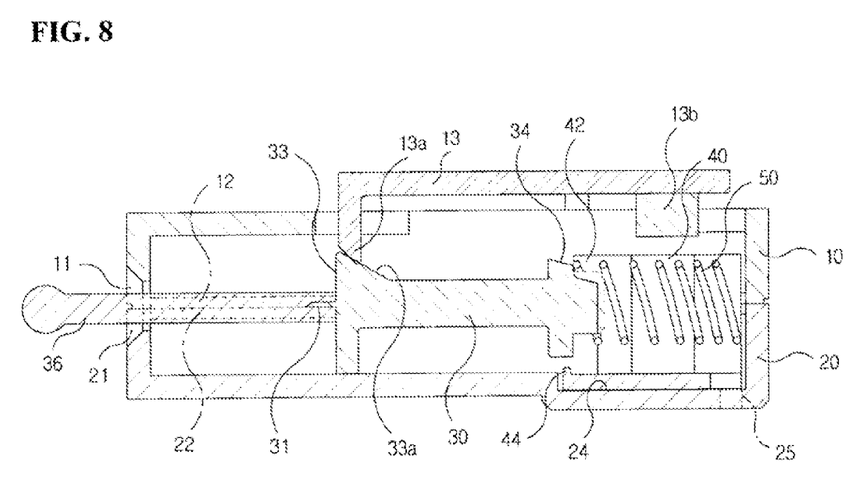
FIG. 8 is a lateral sectional view of a safety lancet according to the present disclosure, showing that it cannot be reloaded.

When blood collection has been performed once as above, should the moving block 30 he pushed once more using the protective cap 36 for attempted reuse, as shown in FIG. 8, after the moving block 30 moves a certain distance rearward, it will he prevented from moving rearward any further when its rear end 34 is caught on the anti-reverse ledge 42 of the guide 40 that has already descended.

Specifically, because the guide 40 is prevented from ascending again when the resilient wings 41 at both sides thereof catch in the insert holes 26. its lowered state is maintained, thus restricting rearward movement of the moving block 30.

Therefore, the safety lancet of the present disclosure is rendered fundamentally non-reusable after it is used once.

A color such as red may he formed on the undersurface of the guide 40 to allow checking of whether the product has been used, so that a user can check the position of the guide 40 through the positioning holes 25 and determine that products whose guides 40 have descended have already been used.

The above safety lancet according to the present disclosure has the effect of fundamentally preventing the possibility of infections from repeated use, because it is rendered non-reusable after being used once to collect blood.

In particular, because the forward movement of the lancet needle is ensured by the guide structure of the moving block that moves forward during the blood collection process, the pain when the lancet needle pierces the skin can be reduced.

Also, because the guide that is positioned at the rear after the safety lancet is used once descends to the floor where it remains. it performs the function of restricting reverse movement of the moving block, so that the lancet cannot be reused without being disassembled, thus improving product reliability.

Although embodiments have been described with reference to a number of illustrative embodiments thereof, it should be understood that numerous other modifications and embodiments can he devised by those skilled in the art that will fall within the spirit and scope of the principles of this disclosure.

Such modified embodiments, however, should not be construed as being separate from the technical spirit and scope of this disclosure, and rather, such modified embodiments should be interpreted as being included in the scope of the following appended claims.

What is claimed is:

1. A safety lancet for preventing reuse, comprising:
   an upper case and a lower case coupled to one another to define a space of a certain volume therein, and defining through-holes at a front end thereof to enable a lancet needle to be exposed therethrough;
   a moving block provided to be movable within the cases and including the lancet needle formed at a front end thereof;
   a guide disposed at a rear end of the moving block within the cases, and including an anti-reverse ledge at a front end thereof to selectively restrict reverse movement for reloading of the moving block;
   a pressing plate pivotably mounted to the upper case on a pivot support that is an axis, and including a stopper projecting downward at a front end thereof on which the moving block is caught, and a pressing projection at a rear end thereof for pressing the guide;
   a seating recess defined in a bottom surface of the lower case, in which the guide that is pressed by the pressing plate descends and is seated and is prevented from ascension; and
   a resilient spring for supporting the rear end of the moving block with a predetermined resilient force, wherein
   the moving block further includes guide projections projecting from either sidewall thereof, and the cases further include guide grooves defined horizontally in inner walls thereof corresponding to the guide projections to guide the guide projections.

2. A safety lancet for preventing reuse, comprising:
   an upper case and a lower case coupled to one another to define a space of a certain volume therein, and defining through-holes at a front end thereof to enable a lancet needle to be exposed therethrough;
   a moving block provided to be movable within the cases and including the lancet needle formed at a front end thereof;
   a guide disposed at a rear end of the moving block within the cases, and including an anti-reverse ledge at a front end thereof to selectively restrict reverse movement for reloading of the moving block;
   a pressing plate pivotably mounted to the upper case on a pivot support that is an axis, and including a stopper projecting downward at a front end thereof on which the moving block is caught, and a pressing projection at a rear end thereof for pressing the guide;
   a seating recess defined in a bottom surface of the lower case, in which the guide that is pressed by the pressing plate descends and is seated; and
   a resilient spring for supporting the rear end of the moving block with a predetermined resilient force, wherein
   the guide further includes resilient wings having a predetermined resiliency projecting from either side thereof, and the seating recess of the lower case defines insert holes in sidewalls thereof corresponding to the resilient wings, for the resilient wings to be inserted therein and prevent ascending of the guide.

3. The safety lancet of claim 1, wherein the guide further includes a connecting ledge at a lower front end thereof, for implementing a connected state with the moving block.

4. The safety lancet of claim 2, wherein the guide further includes a connecting ledge at a lower front end thereof, for implementing a connected state with the moving block.

5. A safety lancet for preventing reuse, comprising:
   an upper case and a lower case coupled to one another to define a space of a certain volume therein, and defining through-holes at a front end thereof to enable a lancet needle to be exposed therethrough;
   a moving block provided to be movable within the cases and including the lancet needle formed at a front end thereof;
   a guide disposed at a rear end of the moving block within the cases, and including an anti-reverse ledge at a front end thereof to selectively restrict reverse movement for reloading of the moving block;
   a pressing plate pivotably mounted to the upper case on a pivot support that is an axis, and including a stopper projecting downward at a front end thereof on which the moving block is caught, and a pressing projection at a rear end thereof for pressing the guide;
   a seating recess defined in a bottom surface of the lower case, in which the guide that is pressed by the pressing plate descends and is seated and is prevented from ascension; and
   a resilient spring for supporting the rear end of the moving block with a predetermined resilient force, wherein
   the seating recess of the lower case defines a positioning hole through a floor thereof, for checking a position of the guide.

6. The safety lancet of claim 5, wherein the moving block defines an inclined surface of a predetermined angle on a top surface at the front end thereof to raise the stopper during reverse movement.

7. A safety lancet for preventing reuse, comprising:
   an upper case and a lower case coupled to one another to define a space of a certain volume therein, and defining through-holes at a front end thereof to enable a lancet needle to be exposed therethrough;
   a moving block provided to be movable within the cases and including the lancet needle formed at a front end thereof;
   a guide disposed at a rear end of the moving block within the cases, and including an anti-reverse ledge at a front end thereof to selectively restrict reverse movement for reloading of the moving block;
   a pressing plate pivotably mounted to the upper case on a pivot support that is an axis, and including a stopper projecting downward at a front end thereof on which the moving block is caught, and a pressing projection at a rear end thereof for pressing the guide;

a seating recess defined in a bottom surface of the lower case, in which the guide that is pressed by the pressing plate descends and is seated and is prevented from ascension; and a resilient spring for supporting the rear end of the moving block with a predetermined resilient force, wherein the moving block further includes a support projection projecting at the rear end thereof on which a front end of the resilient spring is inserted and supported, and the lower case includes a supporting partition of a predetermined height to provide positioning support at a rear end of the resilient spring.

8. The safety lancet of claim 7, wherein the guide further includes a recess defined in the rear end thereof to prevent interference with the supporting partition during reversal.

* * * * *